(12) United States Patent
Mishima et al.

(10) Patent No.: US 9,592,330 B2
(45) Date of Patent: Mar. 14, 2017

(54) DIALYSIS APPARATUS

(71) Applicant: Shibuya Kogyo Co., Ltd., Kanazawa-shi, Ishikawa (JP)

(72) Inventors: Takashi Mishima, Kanazawa (JP); Shingo Saito, Kanazawa (JP)

(73) Assignee: SHIBUYA KOGYO CO., LTD., Kanazawa-shi, Ishikawa (JP)

( * ) Notice: Subject to any disclaimer, the term of this patent is extended or adjusted under 35 U.S.C. 154(b) by 85 days.

(21) Appl. No.: 14/416,501

(22) PCT Filed: Jun. 17, 2013

(86) PCT No.: PCT/JP2013/066550
§ 371 (c)(1),
(2) Date: Jan. 22, 2015

(87) PCT Pub. No.: WO2014/017214
PCT Pub. Date: Jan. 30, 2014

(65) Prior Publication Data
US 2015/0174310 A1    Jun. 25, 2015

(30) Foreign Application Priority Data

Jul. 26, 2012 (JP) .................................. 2012-166278

(51) Int. Cl.
*A61M 1/16* (2006.01)
*B01D 19/00* (2006.01)

(52) U.S. Cl.
CPC ........ *A61M 1/1658* (2013.01); *A61M 1/1686* (2013.01); *A61M 1/1688* (2014.02); *B01D 19/0042* (2013.01)

(58) Field of Classification Search
CPC .............. A61M 1/1658; A61M 1/1686; A61M 1/1688; B01D 19/0042
See application file for complete search history.

(56) References Cited

U.S. PATENT DOCUMENTS

| 3,738,382 A | 6/1973 | Cappelen, Jr. et al. |
| 3,976,574 A | 8/1976 | White |

(Continued)

FOREIGN PATENT DOCUMENTS

| JP | 50-11866 B1 | 5/1975 |
| JP | 63-38885 Y2 | 12/1986 |

(Continued)

OTHER PUBLICATIONS

Form PCT/ISA/210 International Search Report issued in Application No. PCT/JP2013/066550 with English translation dated Jul. 30, 2013 (5 pages).

(Continued)

*Primary Examiner* — John Kim
(74) *Attorney, Agent, or Firm* — Flynn, Thiel, Boutell & Tanis, P.C.

(57) ABSTRACT

A dialysis apparatus has a dialysate circuit 4 which is cleaned after dialysis by both opening/closing valves V101 and V102 being closed after a dialysate in the dialysate circuit 4 is replaced with a cleaning liquid. The opening/closing valve V12 is opened, and the cleaning liquid is circulated by pumps P1 and P4 while being heated by a heater H1, to clean the inside of the dialysate circuit 4. A deaeration tank 31 is provided downstream of the pump P1. Air bubbles generated from the cleaning liquid serving as hot water are deaerated by the deaeration tank 31 and are then discharged into a gas storage tank 48 via a deaeration passage 32. The pumps P1 and P4 can be reliably prevented from being unable to operate with the air bubbles generated from the cleaning liquid.

3 Claims, 3 Drawing Sheets

(56) References Cited

U.S. PATENT DOCUMENTS

| | | | |
|---|---|---|---|
| 5,580,460 A | 12/1996 | Polaschegg | |
| 7,622,043 B2* | 11/2009 | Sawada | A61M 1/169 |
| | | | 210/636 |
| 2011/0220562 A1* | 9/2011 | Beiriger | A61M 1/1696 |
| | | | 210/120 |

FOREIGN PATENT DOCUMENTS

| | | |
|---|---|---|
| JP | 07-024266 A | 1/1995 |
| JP | 3495068 B2 | 3/1995 |
| JP | 2001-009029 A | 1/2001 |
| WO | WO 2011/112317 A1 | 9/2011 |

OTHER PUBLICATIONS

Form PCT/ISA/220 Notification of Transmittal of International Search Report issued in Application No. PCT/JP2013/066550 dated Jul. 30, 2013 (2 pages).
Form PCT/ISA/237 Written Opinion of International Searching Authority issued in Application No. PCT/JP2013/066550 dated Jul. 30, 2013 (3 pages).
European Search Report for corresponding application No. 13823885.2, dated Feb. 10, 2016 (7 pgs.).

\* cited by examiner

DIALYSIS APPARATUS

TECHNICAL FIELD

The present invention relates to a dialysis apparatus, and more specifically, to a dialysis apparatus adapted to clean a dialysate circuit by circulating a heated cleaning liquid therethrough.

BACKGROUND ART

In a hospital where a dialysis apparatus subjects a patient to dialysis treatment, a dialysate circuit is cleaned at a required timing such as a time point where one day ends or treatment for one patient ends. Conventionally, a technique for cleaning a liquid circuit by circulating hot water therethrough has been known (e.g., Patent Literature 1).

In an apparatus in Patent Literature 1, hot water heated by a heating device 9 is circulated through the liquid circuit in a state where both valves 21 and 24 are closed after the liquid circuit is filled with a cleaning liquid while a valve 26 in a short-circuit 25, which bypasses an inlet pipe 1 and a return circuit distal end 2, is opened.

However, when the heated hot water serving as the cleaning liquid is circulated through the liquid circuit, air bubbles are generated from the hot water. When air bubbles in a large amount are eventually entrained in a pump, a liquid becomes unable to be fed. As a pump in which such a malfunction occurs, a gear pump and a vane pump have been known. Further, as a dialysis apparatus in which the gear pump is arranged in the liquid circuit, Patent Literature 2, for example, has been known.

If the dialysate circuit in the dialysis apparatus is cleaned by circulating the hot water therethrough, the air bubbles generated from the hot water in the dialysate circuit need to be removed to prevent the pump from being unable to feed a liquid. A conventionally general dialysis apparatus includes a deaeration device for deaerating a dialysate. When the inside of the dialysate circuit is cleaned with the hot water, the air bubbles generated from the hot water are also removed using the existing deaeration device. Such a deaeration device is described in Patent Literature 1 (a deaeration device 10), and is also disclosed in Patent Literatures 2 and 3.

PRIOR ART DOCUMENTS

Patent Literature

Patent Literature 1: Japanese Patent Publication No. 50-11866
Patent Literature 2: Japanese Patent No. 3495068
Patent Literature 3: Japanese Utility Model Publication No. 63-38885

SUMMARY OF INVENTION

Problems to be Solved by the Invention

The apparatus in Patent Literature 1 is configured to discharge the air bubbles out of the deaeration device 10 via a gas outlet 30 provided with a relief valve 31 in the deaeration device 10.

On the other hand, when a deaeration tank disclosed in Patent Literature 3 is used to clean a dialysate circuit in a dialysis apparatus, hot water, together with air bubbles is also discharged outward. Thus, the dialysate circuit is gradually depressurized. When the dialysate circuit is thus depressurized, a boiling point of the hot water within the dialysate circuit decreases. Thus, an amount in which the air bubbles are generated from the hot water also increases, and thus a pump becomes unable to feed a liquid by entraining the air bubbles therein.

The present invention is directed to reliably preventing a pump from being unable to feed a liquid with air bubbles generated from a cleaning liquid.

Means for Solving the Problems

In view of the above-mentioned circumstances, the present invention (1) provides a dialysis apparatus including a dialysate circuit that supplies a dialysate to a dialyzer and recovers a treated dialysate, the dialysate circuit including a liquid supply passage that introduces a dialysate or a required liquid into the dialysate circuit, a liquid discharge passage that discharges the treated dialysate out of the dialysis circuit, a circulation passage that connects the liquid supply passage and the liquid discharge passage, a pump that is provided in the liquid supply passage and feeds the liquid in the liquid supply passage toward the downstream side, a liquid supply passage opening/closing valve that is provided upstream of a connection portion with the circulation passage in the liquid supply passage and opens and closes the liquid supply passage, a liquid discharge passage opening/closing valve that is provided downstream of a connection portion with the circulation passage in the liquid discharge passage and opens and closes the liquid discharge passage, a deaeration tank that is provided in the liquid supply passage and removes gas from the liquid within the liquid supply passage, a deaeration passage that has its one end connected to the deaeration tank and discharges the gas removed by the deaeration tank, and heating means that heats the liquid within the dialysate circuit, in which the liquid supply passage opening/closing valve and the liquid discharge passage opening/closing valve are closed after the cleaning liquid is introduced into the dialysate circuit, and in the state, the cleaning liquid in the dialysate circuit is heated while being circulated by the pump to clean the dialysate circuit, a gas storage unit is provided in the liquid discharge passage between the connection portion with the circulation passage in the liquid discharge passage and the liquid discharge passage opening/closing valve, to store the gas discharged from the other end of the deaeration passage in it.

The present invention (2) premises a configuration described in (1), in which the gas storage unit includes a gas storage tank provided in the liquid discharge passage, a connection port provided in an upper part of the gas storage tank is connected to the downstream side of the liquid discharge passage while a connection port provided in a lower part of the gas storage tank is connected to the upstream side of the liquid discharge passage, the gas discharged from the other end of the deaeration passage is introduced into the gas storage tank via the connection port provided in the upper part of the gas storage tank.

Advantageous Effects of Invention

According to the invention (1), the air bubbles generated when the heated cleaning liquid is circulated is discharged into the gas storage unit from the deaeration tank via the deaeration passage and is stored therein. Thus, the air bubbles are prevented from being entrained in the pump so that the pump can reliably be prevented from being unable to feed a liquid.

According to the invention (2), the cleaning liquid is fed to the gas storage tank from the liquid discharge passage via the connection port in the lower part of the gas storage tank, and the cleaning liquid and air can be discharged into a distal end of the liquid discharge passage via the connection port in the upper part of the gas storage tank. Thus, the inside of the gas storage tank can be cleaned with the cleaning liquid.

BRIEF DESCRIPTION OF DRAWINGS

FIG. 2(a) illustrates a state during normal dialysis treatment, and FIG. 2(b) illustrates the time of cleaning a dialysate circuit.

MODE FOR CARRYING OUT THE INVENTION

Figure 1:
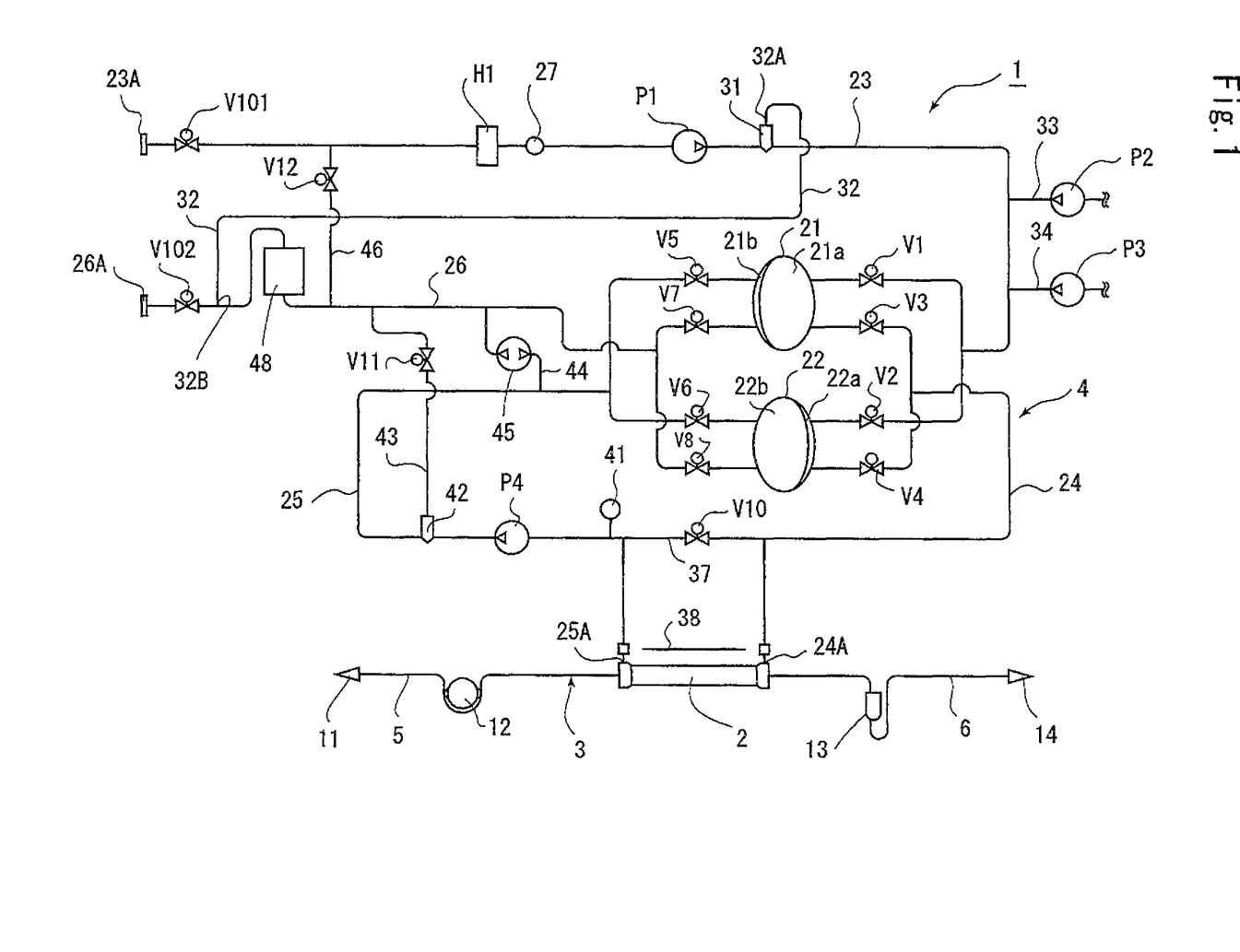
FIG. 1 is a configuration diagram illustrating an embodiment of the present invention.

The present invention will be described below for an illustrated embodiment. In FIG. 1, reference numeral 1 denotes a dialysis apparatus for subjecting a patient to dialysis treatment. This dialysis apparatus 1 includes a dialyzer 2 that performs hemodialysis, a blood circuit 3 connected to the dialyzer 2, and a dialysate circuit 4 connected to the dialyzer 2. Control means (not illustrated) controls the components in the dialysis apparatus 1.

The dialyzer 2 has conventionally been well-known. The inside of the dialyzer 2 is partitioned into a blood chamber and a dialysate chamber through a hollow fiber membrane (not illustrated). Blood flows through the blood chamber while a dialysate flows through the dialysate chamber.

The blood circuit 3 includes an artery-side passage 5 connected to the artery of the patient and connected to one end of the dialyzer 2, and a vein-side passage 6 connected to the vein of the patient and connected to the other end of the dialyzer 2.

The artery-side passage 5 includes a puncture needle 11 that punctures the patient, a blood pump 12 composed of a tube pump that feeds the blood, and clamping means and a pressure gauge (not illustrated). On the other hand, the vein-side passage 6 includes a drip chamber 13 that eliminates air from the blood and a puncture needle 14 that punctures the patient while the drip chamber 13 includes a pressure gauge (not illustrated).

On the other hand, the dialysate circuit 4 includes first and second dialysate chambers 21 and 22 having the same shape that supply and discharge the dialysate, a liquid supply passage 23 that supplies pure water or a cleaning liquid to the first and second dialysate chambers 21 and 22, a dialysate supply passage 24 that supplies a fresh dialysate to the dialyzer 2 from the first and second dialysate chambers 21 and 22, a dialysate recovery passage 25 that recovers the used dialysate, which has passed through the dialyzer 2, in the first and second dialysate chambers 21 and 22, and a liquid discharge passage 26 that discharges the used dialysate to a liquid discharge tank (not illustrated) from the first and second dialysate chambers 21 and 22.

In the present embodiment, the control means (not illustrated) controls all of a plurality of pumps and a plurality of opening/closing valves provided in the dialysate circuit 4, described below.

The inside of each of the first dialysate chamber 21 and the second dialysate chamber 22 is partitioned by one diaphragm so that supply chambers 21a and 22a containing the fresh dialysate and recovery chambers 21b and 22b containing the used dialysate are formed.

An upstream end 23A of the liquid supply passage 23 is connected to a liquid supply source (not illustrated), and a downstream portion in the liquid supply passage 23 is branched into branch portions in two directions, and the branch portions are respectively connected to the supply chambers 21a and 22a in the first and second dialysate chambers 21 and 22. The two branch portions are respectively provided with liquid supply valves V1 and V2.

Figure 3:
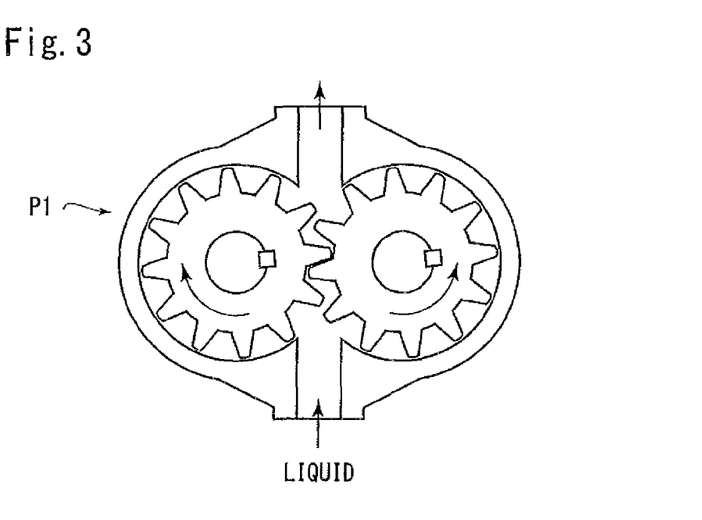
FIG. 3 is a cross-sectional view of a pump illustrated in FIG. 1.

An opening/closing valve V101 for opening and closing the liquid supply passage 23 is provided in a part, close to the upstream end 23A, of the liquid supply passage 23, is provided with a heater H1, a thermometer 27, a deaeration pump P1, and a deaeration tank 31 arranged at positions sequentially downstream of the opening/closing valve V101 in the liquid supply passage 23. The opening/closing valve V101 is opened or closed at a required time, to open or close the liquid supply passage 23. The heater H1 can heat a liquid flowing through the liquid supply passage 23 to a required temperature. The thermometer 27 measures a temperature of the liquid flowing through the liquid supply passage 23. The temperature of the measured liquid is transmitted to the control means. The deaeration pump P1 includes a conventionally known gear pump, as illustrated in FIG. 3, so that the liquid is fed from the upstream side to the downstream side using a pair of gears when driven to rotate at the required time by the control means.

Figure 2:
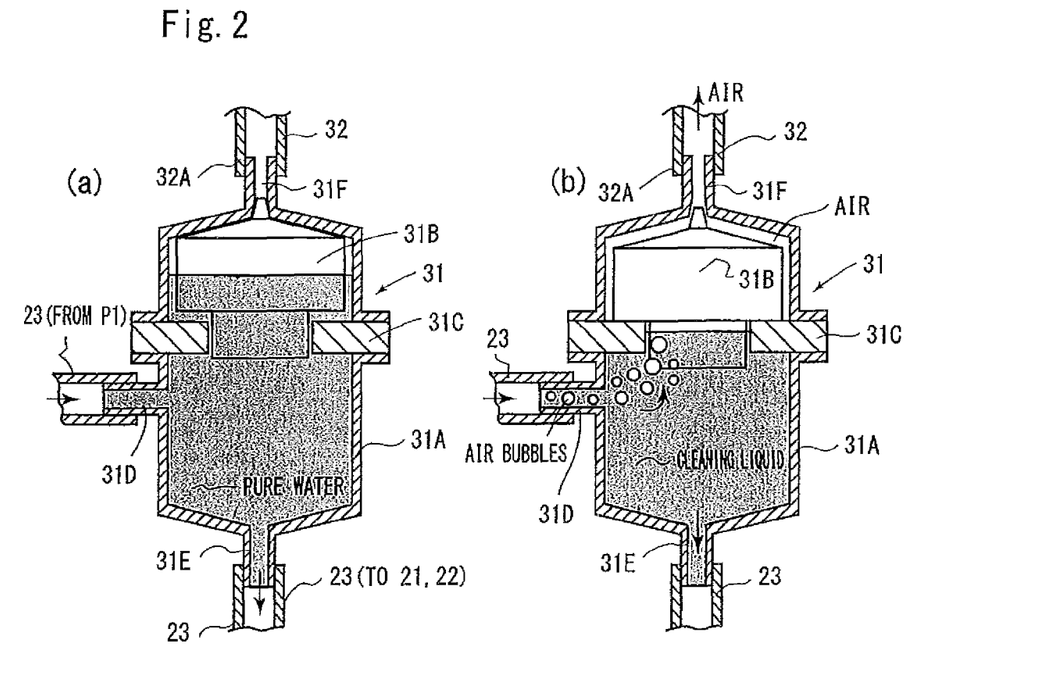
FIG. 2 is a cross-sectional view of a deaeration tank illustrated in FIG. 1, where

Then, as illustrated in FIG. 2, the deaeration tank 31 includes a casing 31A in a schematically cylindrical shape, a float 31B arranged in an upper part of the casing 31A, and a spacer 310 arranged in an upper inner peripheral part of the casing 31A. The float 31B has a shape of a stepped pillar, and the spacer 31C regulates a position at a descent end of the float 31B in the casing 31A (see FIG. 2(b)).

A connection port 31D is formed on a side surface of the casing 31A, and the upstream side of the liquid supply passage 23 on the side of the deaeration pump P1 is connected to the connection port 31D. A connection port 31E is formed on a bottom surface of the casing 31A, and the downstream side of the liquid supply passage 23 leading to both the chambers 21 and 22 is connected to the connection port 31E. Further, a connection port 31F is formed on a top surface of the casing 31A, and one end 32A of the deaeration passage 32 is connected to the connection port 31F.

When the deaeration pump P1 is driven to rotate with the opening/closing valve V101 opened, pure water (RO (Reverse Osmosis) water) in a liquid supply source is introduced into the liquid supply passage 23 via the upstream end 23A and is fed to both the chambers 21 and 22 by the pump P1. Correspondingly, the pure water flows through the deaeration tank 31. More specifically, the pure water is introduced into the deaeration tank 31 via the connection port 31D while being fed to both the chambers 21 and 22 by flowing toward the downstream side of the liquid supply passage 23 from the connection port 31E at the bottom. When the pure water thus flows through the deaeration tank 31, the float 31B is raised to an ascent end due to the pure water in the deaeration tank 31. Thus, a small-diameter portion at an upper end of the float 31B is fitted into the connection port 31F, to completely close the connection port 31F. On the other hand, if air bubbles exist in a heated cleaning liquid when the cleaning liquid flows through the deaeration tank 31 during cleaning of the dialysate circuit 4, described below, the air bubbles float upward, and are stored in an upper part of the casing 31A. Thus, the float 31B falls as the liquid level of the cleaning liquid falls, and is supported on the spacer 31C (see FIG. 2(b)). If the float 31B thus falls, the connection port 31F on the top surface is opened. Thus, air in an upper space of the deaeration tank 31 is discharged out of the deaeration tank 31 via the connection port 31F and the deaeration passage 32 connected thereto.

Furthermore, respective ends of a B liquid supply passage 33 and an A liquid supply passage 34 are sequentially connected to the liquid supply passage 23 downstream of the deaeration tank 31. The liquid supply passages 33 and 34 are respectively provided with pumps P2 and P3. The pumps P2 and P3 are driven to rotate when the pure water is being fed in the liquid supply passage 23 so that an A liquid and a B liquid are mixed with the pure water in the liquid supply passage 23 via the B liquid supply passage 33 and the A liquid supply passage 34, to prepare a fresh dialysate.

Then, an upstream portion of the dialysate supply passage 24 is branched into branch portions in two directions, and the branch portions are respectively connected to the supply chambers 21a and 22a in the first and second dialysate chambers 21 and 22, and a coupler 24A detachably connected to the dialyzer 2 is provided at its downstream end. The branch portions are respectively provided with supply valves V3 and V4.

On the other hand, a coupler 25A detachably connected to the dialyzer 2 is provided at an upstream end of the dialysate recovery passage 25, and a downstream portion of the dialysate recovery passage 25 is branched into branch portions in two directions, and the branch portions are respectively connected to the recovery chambers 21b and 22b in the first and second dialysate chambers 21 and 22.

A dialysate pump P4, which feeds a dialysate to the downstream side, is provided upstream of the branch portions in the dialysate recovery passage 25 while the branch portions are respectively provided with recovery valves V5 and V6. The dialysate pump P4 includes a gear pump, illustrated in FIG. 3, similarly to the deaeration pump P1 in the liquid supply passage 23.

An upstream portion of the liquid discharge passage 26 is branched into branch portions in two directions, and the branch portions are respectively connected to the recovery chambers 21b and 22b in the first and second dialysate chambers 21 and 22, and its lower end 26A is connected to a tank (not illustrated). The branch portions are respectively provided with liquid discharge valves V7 and V8. An opening/closing valve V102, which opens and closes the liquid discharge passage 26, is provided at a position adjacent to a downstream end 26A of the liquid discharge passage 26, and the control means opens and closes the opening/closing valve V102 at a required time.

Furthermore, a first bypass passage 37, which makes the dialysate supply passage 24 and the dialysate recovery passage 25 communicate with each other, is provided. The first bypass passage 37 is provided with an opening/closing valve V10. While the opening/closing valve V10 is closed when dialysis treatment is performed, the dialysate supply passage 24 and the dialysate recovery passage 25 communicate with each other via the first bypass passage 37 when the control means opens the opening/closing valve V10 at the required time.

Furthermore, a second bypass passage 38 is arranged at a position in closer proximity to the dialyzer 2 than the first bypass passage 37. The second bypass passage 38 is connected to the dialysate supply passage 24 and the dialysate recovery passage 25 when the dialysate circuit 4 is cleaned, although not connected to the dialysate supply passage 24 and the dialysate recovery passage 25 when dialysis treatment is performed. That is, the coupler 24A is detached from the dialyzer 2 and is connected to one end of the second bypass passage 38, and the coupler 25A is detached from the dialyzer 2 and is connected to the other end of the second bypass passage 38 so that the dialysate supply passage 24 and the dialysate recovery passage 25 are connected to each other via the bypass passage 38.

Then, the dialysate recovery passage 25 is provided with a pressure sensor 41, which measures pressure, the dialysate pump P4, which feeds a dialysate to the downstream side, and an air removal tank 42, which removes air in the dialysate, in this order from the dialyzer 2. The air removal tank 42 is provided with a third bypass passage 43, which makes the dialysate recovery passage 25 and the liquid discharge passage 26 communicate with each other, and the third bypass passage 43 is provided with an opening/closing valve V11. The opening/closing valve V11 is opened at a required time during dialysis treatment so that the air removed from the liquid by the air removal tank 42 is discharged to the liquid discharge passage 26 via the third bypass passage 43. A fourth bypass passage 44, which makes the dialysate recovery passage 25 and the liquid discharge passage 26 communicate with each other, is provided downstream of the air removal tank 42, and the fourth bypass passage 44 is provided with a water removal pump 45 for removing water during dialysis treatment.

Over the liquid discharge passage 26 positioned between its connection part with the third bypass passage 43 and the opening/closing valve V102 and the liquid supply passage 23 slightly downstream of the opening/closing valve V101, a fifth bypass passage 46, which makes both the passages 23 and 26 communicate with each other, is provided, and the fifth bypass passage 46 is provided with an opening/closing valve V12. The opening/closing valve V12 is closed during dialysis treatment. On the other hand, the opening/closing valve V12 is opened when the dialysate circuit 4 is cleaned. In this case, the passages 23 and 26 communicate with each other via the fifth bypass passage 46 serving as a circulation passage.

A configuration of the dialysis apparatus 1, so far described, is similar to a conventionally known configuration. The present embodiment is characterized in that when the inside of the dialysate circuit 4 is cleaned with the cleaning liquid, the deaeration tank 31 first deaerates the cleaning liquid, and air within the deaeration tank 31 is then discharged to a gas storage tank 48 via the deaeration passage 32 and the liquid discharge passage 26, and stored therein on the premise of the above-mentioned configuration.

More specifically, one end 32A of the deaeration passage 32 is connected to the connection port 31F in the deaeration tank 31, as described above. On the other hand, the other end 32B of the deaeration passage 32 is connected to a part, adjacent to and upstream of the opening/closing valve V102, of the liquid discharge passage 26. The gas storage tank 48 is provided in the liquid discharge passage 26 positioned between a connection part with the other end 32B of the deaeration passage 32 and a connection part with the fifth bypass passage 46.

Figure 4:
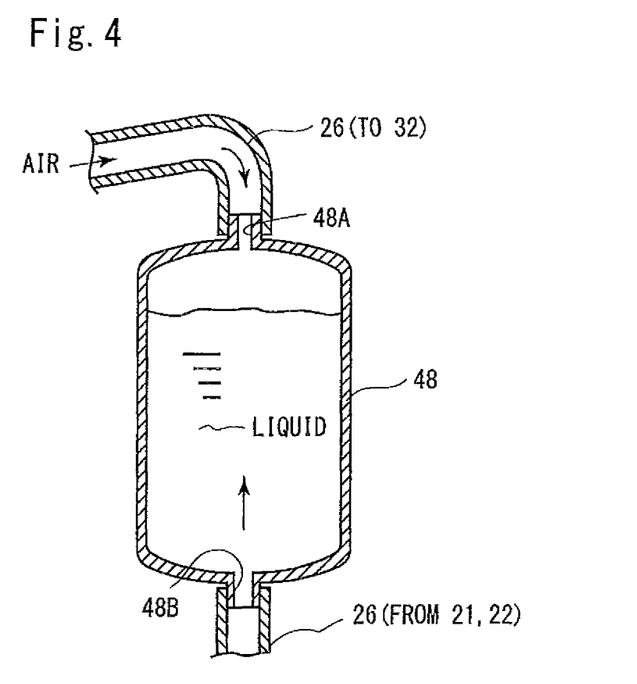
FIG. 4 is a longitudinal sectional view of a gas storage tank illustrated in FIG. 1.

As illustrated in FIG. 4, the gas storage tank 48 has a configuration in which the float 31B in the deaeration tank 31 and the connection port 31D on its side surface, as illustrated in FIG. 2, are omitted. More specifically, the gas storage tank 48 is formed in a shape of a cylinder whose top and bottom surfaces are closed, and the downstream side of the liquid discharge passage 26 communicating with the deaeration passage 32 is connected to a connection port 48A on the top surface. On the other hand, the upstream side of the liquid discharge passage 26 communicating with both the chambers 21 and 22 is connected to a connection port 48B on the bottom surface of the gas storage tank 48.

The gas storage tank 48 is supported in a vertical direction so that the connection port 48A is in its upper part and the connection port 48B is in its lower part. Thus, during dialysis treatment, a treated dialysate is introduced into the gas storage tank 48 via the lower connection port 48B, and is discharged into the liquid discharge passage 26 on the downstream side via the connection port 48A on the top surface when the inside of the gas storage tank 48 becomes full.

On the other hand, air bubbles generated in the cleaning liquid within the liquid supply passage 23 during cleaning of the dialysate circuit 4 are accumulated in the deaeration tank 31, as illustrated in FIG. 2(b), and air accumulated within the deaeration tank 31 is discharged into the liquid discharge passage 26 via the deaeration passage 32. The opening/closing valve V102 is closed during the cleaning of the dialysate circuit 4, as described below. Thus, air discharged from the deaeration passage 32 to the liquid discharge passage 26 is stored in the gas storage tank 48 from the upper connection port 48A of the gas storage tank 48 after flowing through the liquid discharge passage 26 (see FIG. 4).

In the above-mentioned configuration, an operation performed when the dialysis apparatus 1 performs dialysis treatment will first be described, and an operation performed when the dialysate circuit 4 is cleaned after the dialysis treatment will be then described. The configuration of the dialysis apparatus 1 is the same as a configuration of a conventionally known dialysis apparatus except that the other end 32B of the deaeration passage 32 is connected to the liquid discharge passage 26 to store air in the gas storage tank 48, as described above. The operation of the dialysis apparatus 1 during dialysis treatment by the dialysis apparatus 1 will be described as simply as possible. As described above, the control means controls an operation of each of the valves V1 to V8, V10 to V12, V101 and V102 in the dialysate circuit 4 and an operation of each of the pumps P1 to 24 and the heater H1, as described above.

The operation during the dialysis treatment will be described. In a state where the opening/closing valve V12 is closed and both the couplers 24A and 25A connect the dialysate circuit 4 to the dialyzer 2, the deaeration pump P1 in the liquid supply passage 23 and the dialysate pump P4 in the dialysate recovery passage 25 are operated while the pumps P2 and P3 in both the supply passages 33 and 34 are operated. Thus, pure water is introduced into the liquid supply passage 23 from the upstream end 23A and is fed toward the downstream side by the deaeration pump P1 while an A liquid and a B liquid are mixed with the pure water in the liquid supply passage 23, to prepare a fresh dialysate.

In this state, in the first dialysate chamber 21, the liquid supply valve V1 and the liquid discharge valve V7 are opened, and the supply valve V3 and the recovery valve V5 are closed. Consequently, the fresh dialysate flows into the supply chamber 21a in the first dialysate chamber 21 from the liquid supply passage 23. Thus, a diaphragm is deformed so that the volume of the recovery chamber 21b decreases. Therefore, a used dialysate contained in the recovery chamber 21b is discharged outward via the liquid discharge passage 26. At this time, the gas storage tank 48 provided in the liquid discharge passage 26 substantially constitutes a part of the liquid discharge passage 26. The dialysate introduced from the lower connection port 48B is discharged from the upper connection port 48A after the gas storage tank 48 is filled with the dialysate, as described above (see FIG. 4).

On the other hand, in the second dialysate chamber 22, the supply valve V4 and the recovery valve V6 are opened, and the liquid supply valve V2 and the liquid discharge valve V8 are closed. Consequently, the used dialysate flows into the recovery chamber 22b. Thus, a diaphragm is deformed so that the volume of the supply chamber 22a decreases. Therefore, a fresh dialysate contained in the supply chamber 22a is supplied to the dialyzer 2 after flowing through the dialysate supply passage 24.

Then, the liquid supply valves V1 and V2, the supply valves V3 and V4, the recovery valves V5 and V6, and the liquid discharge valves V7 and V8 are alternately opened or closed so that the fresh dialysate is supplied to the dialyzer 2 via the dialysate supply passage 24 from the first and second dialysate chambers 21 and 22. The used dialysate, which has passed through the dialyzer 2, is recovered in the first and second dialysate chambers 21 and 22 via the dialysate recovery passage 25, and is then discharged outward via the liquid discharge passage 26 and the downstream end 26A thereof.

The dialysate is supplied to the dialyzer 2 by the dialysate circuit 4 in the above-mentioned manner while the used dialysate is recovered from the dialyzer 2, to subject a patient to dialysis treatment. However, in the case of the dialysis treatment, an upper part of the deaeration tank 31 is filled with the dialysate, as illustrated in FIG. 2(a). Thus, the connection port 31F of the deaeration tank 31 is closed by an upper end of the float 31B (see FIG. 2(a)). The heater H1 is operated during the dialysis treatment. Thus, air bubbles are accumulated in the deaeration tank 31. If air bubbles in a predetermined amount or more are stored in the deaeration tank 31, however, the air bubbles are discharged from the deaeration tank 31, as illustrated in FIG. 2(b).

If the dialysis apparatus 1 performs the dialysis treatment in the above-mentioned manner, the inside of the dialysate circuit 4 is cleaned in the following manner. That is, retransfusion processing for returning blood remaining in the blood circuit 3 to the patient is first performed after the end of the dialysis treatment. When the retransfusion is finished, both the couplers 24A and 25A are detached from the dialyzer 2 and are connected to the second bypass passage 38. Thus, the dialysate supply passage 24 and the dialysate recovery passage 25 communicate with each other via the second bypass passage 38.

Then, the deaeration pump P1 and the dialysate pump P4 are operated, to start to introduce pure water into the dialysate circuit 4 from the upstream end 23A of the liquid supply passage 23 while raising the temperature of the heater H1 to a cleaning temperature (about 90° C.). Correspondingly, each of the valves V1 to V8 and V10 to V12 is opened or closed, as needed, to replace the dialysate remaining within the dialysate circuit 4 with the pure water.

If the pure water is supplied to the dialysate circuit 4 only for a predetermined period of time, the opening/closing valves V101 and V102 are closed to seal the dialysate circuit 4 while the opening/closing valve V12 is opened. Thus, the dialysate circuit 4 is formed as a closed circuit for cleaning via the fifth bypass passage 46 serving as a circulation passage and the second bypass passage 38.

Then, the deaeration pump P1 and the dialysate pump P4 are driven only for a set period of time, to circulate the heated pure water within the closed circuit for cleaning. In this case, each of the valves V1 to V8 and V10 to V12 is opened or closed, as needed, so that hot water is also caused to flow through the first bypass passage 37, the third bypass passage 43, and the fourth bypass passage 44, to clean their respective inner parts.

While the dialysate circuit 4 is thus being cleaned, air bubbles occur within the hot water generated by heating. However, the deaeration tank 31 in the liquid supply passage 23 removes the air bubbles within the hot water (see FIG. 2(b)). The air that has accumulated in the deaeration tank 31 is introduced into the gas storage tank 48 from the upper connection port 48A via the deaeration passage 32 and the liquid discharge passage 26. Thus, the air bubbles generated within the hot water are captured by the deaeration tank 31, then discharged into the gas storage tank 48 via the deaeration passage 32, and are stored therein. Therefore, the air bubbles generated within the hot water can reliably be prevented from being entrained in the deaeration pump P1.

The opening/closing valve V12 is temporarily closed while the opening/closing valve V11 and the opening/closing valve V102 are temporarily opened during the cleaning work. Thus, the hot water is introduced into the gas storage tank 48 via the lower connection port 48B and discharged therefrom via the upper connection port 48A. Therefore, the air is discharged from within the gas storage tank 48 while the inside of the gas storage tank 48 is cleaned with the hot water.

Then, when a previously set cleaning period of time is finished, operations of the heater H1, the deaeration pump P1, and the dialysate bump P4 are stopped, to end the cleaning work.

According to the above-mentioned embodiment, the air bubbles generated from the heated cleaning liquid (hot water) can be discharged into the gas storage tank 48 via the deaeration tank 31 and the deaeration passage 32. Thus, the deaeration pump P1 and the dialysate pump P4, which feed the cleaning liquid, can reliably be prevented from being unable to feed the liquid by preventing the air bubbles from being entrained in the deaeration pump P1 and the dialysate pump P4. Therefore, the inside of the dialysate circuit 4 can reliably be cleaned by efficiently circulating the hot water within the dialysate circuit 4.

During the cleaning, the air, which has accumulated in the gas storage tank 48, together with the cleaning liquid, is discharged out of the gas storage tank 48 so that the inside of the gas storage tank 48 can also be cleaned.

In the above-mentioned embodiment, the present invention is applied to a system for mixing the A liquid and the B liquid with the pure water within the dialysis apparatus 1 to prepare the fresh dialysate. However, the present invention is also applicable to a dialysis apparatus using a system for supplying a fresh dialysate that has already been prepared using a dialysate preparation device (a so-called dialysis monitoring device or console). In this case, the A liquid supply passage 33, the B liquid supply passage 34, and both the pumps P2 and P3 can be omitted, and the fresh dialysate or the pure water is supplied from the liquid supply passage 23.

While a gear pump is used as the deaeration pump P1 and the dialysate pump P4 in the above-mentioned embodiment, the gear pump may be replaced with a pump using a system of making a liquid unable to be fed by entraining air therein, e.g., a vane pump.

REFERENCE SIGNS LIST

1 . . . dialysis apparatus
2 . . . dialyzer
4 . . . dialysate circuit
23 . . . liquid supply passage
26 . . . liquid discharge passage
31 . . . deaeration tank
32 . . . deaeration passage
46 . . . fifth bypass passage (circulation passage)
48 . . . gas storage tank (gas storage unit)
H1 . . . heater
V101 . . . opening/closing valve (liquid supply passage opening/closing valve)
V102 . . . opening/closing valve (liquid discharge passage opening/closing valve)

The invention claimed is:

1. A dialysis apparatus comprising a dialysate circuit that supplies a dialysate to a dialyzer and recovers a treated dialysate, the dialysate circuit comprising a liquid supply passage that introduces a dialysate or a required liquid into the dialysate circuit, a liquid discharge passage that discharges the treated dialysate out of the dialysis circuit, a circulation passage that connects the liquid supply passage and the liquid discharge passage, a pump that is provided in the liquid supply passage and feeds the liquid in the liquid supply passage towards the downstream side, a liquid supply passage opening/closing valve that is provided upstream of a connection portion with the circulation passage in the liquid supply passage and opens and closes the liquid supply passage, a liquid discharge passage opening/closing valve that is provided downstream of a connection portion with the circulation passage in the liquid discharge passage and opens and closes the liquid discharge passage, a deaeration tank that is provided in the liquid supply passage and removes gas from the liquid within the liquid supply passage, a deaeration passage that has its one end connected to the deaeration tank and discharges the gas removed by the deaeration tank, heating means that heats the liquid within the dialysate circuit, a control means configured to control the aforementioned pump, supply passage opening/closing valve, liquid discharge passage opening/closing valve and the heating means such that the liquid supply passage opening/closing valve and the liquid discharge passage opening/closing valve are closed after the cleaning liquid is introduced into the aforementioned dialysate circuit and, in this state, the cleaning liquid in the dialysate circuit is heated while being circulated by the pump to clean the dialysate circuit, and a gas storage unit provided in the liquid discharge passage between the connection portion with the circulation passage in the liquid discharge passage and the liquid discharge passage opening/closing valve, for storing the gas discharged from the other end of the deaeration passage therein.

2. The dialysis apparatus according to claim 1, wherein the gas storage unit comprises a gas storage tank provided in the liquid discharge passage, a connection port provided in an upper part of the gas storage tank is connected to the downstream side of the liquid discharge passage while a connection port provided in a lower part of the gas storage tank is connected to the upstream side of the liquid discharge passage, the gas discharged from the other end of the deaeration passage is introduced into the gas storage tank via the connection port provided in the upper part of the gas storage tank.

3. The dialysis apparatus according to claim 1, wherein the deaeration tank contains a float having the shape of a stepped pillar and a spacer for regulating a position of a lower portion of the float, an upper portion of the float having a greater diameter than the lower portion of the float and having an upper end configured to prevent flow into the deaeration passage when the heated cleaning liquid does not contain air bubbles and allow air contained in the heated cleaning liquid to be removed therefrom and exit through the deaeration passage when the heated cleaning liquid contains air bubbles.

* * * * *